(12) United States Patent
de Meulenaer et al.

(10) Patent No.: US 6,736,979 B2
(45) Date of Patent: *May 18, 2004

(54) DEVICE AND PROCESS FOR TREATING A LIQUID MEDIUM

(75) Inventors: Eric Cordemans de Meulenaer, Wezembeck-Oppem (BE); Baudouin Hannecart, La Roche-en-Ardenne (BE); Yves Canivet, Evere (BE)

(73) Assignee: Ashland, Inc., Covington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/358,445

(22) Filed: Feb. 4, 2003

(65) Prior Publication Data

US 2003/0132165 A1 Jul. 17, 2003

Related U.S. Application Data

(63) Continuation of application No. 09/214,398, filed as application No. PCT/BE97/00078 on Jul. 4, 1997, now Pat. No. 6,540,922.

(30) Foreign Application Priority Data

Jul. 4, 1996 (BE) .............................................. 09600613

(51) Int. Cl.⁷ .................................................. C02F 1/32
(52) U.S. Cl. .................. 210/695; 204/157.62; 210/696; 210/721; 210/748; 210/758; 210/759; 210/760; 210/764; 210/192; 210/167; 210/195.1; 210/199; 210/205; 210/222; 210/223; 422/20; 422/22; 422/24; 422/28; 422/186.01; 422/186.3; 128/898; 601/2
(58) Field of Search ..................... 128/898; 210/695, 210/696, 721, 738, 748, 758, 759, 760, 763, 764, 167, 192, 195.1, 198.1, 199, 205, 222, 223; 422/20, 22, 24, 28, 186, 186.01, 186.3; 204/157.62; 601/2; 604/22

(56) References Cited

U.S. PATENT DOCUMENTS

| | | | | |
|---|---|---|---|---|
| 2,717,874 A | * | 9/1955 | Verain ........................ 210/748 |
| 3,672,823 A | * | 6/1972 | Boucher ........................ 422/20 |
| 4,003,832 A | * | 1/1977 | Henderson et al. ......... 210/728 |
| 4,076,617 A | * | 2/1978 | Bybel et al. ................. 210/748 |
| 4,144,722 A | * | 3/1979 | Mattwell ....................... 62/305 |
| 4,879,045 A | * | 11/1989 | Eggerichs ................... 210/695 |
| 4,961,860 A | * | 10/1990 | Masri ........................ 210/748 |
| 4,971,991 A | * | 11/1990 | Umemura et al. .......... 514/410 |
| 5,130,031 A | * | 7/1992 | Johnston ..................... 210/748 |
| 5,130,032 A | * | 7/1992 | Sartori ....................... 210/748 |
| 5,198,122 A | | 3/1993 | Koszalka et al. ........... 210/748 |
| 5,215,680 A | * | 6/1993 | D'Arrigo ..................... 516/11 |
| 5,380,411 A | * | 1/1995 | Schlief .................. 204/157.15 |
| 5,558,092 A | * | 9/1996 | Unger et al. ................ 600/439 |
| 5,827,204 A | * | 10/1998 | Grandia et al. ................ 601/2 |
| 6,068,857 A | * | 5/2000 | Weitschies et al. ......... 424/489 |
| 6,308,714 B1 | * | 10/2001 | Peterson et al. ............ 128/898 |
| 6,309,355 B1 | * | 10/2001 | Cain et al. .................. 600/439 |
| 6,413,216 B1 | * | 7/2002 | Cain et al. .................. 600/439 |
| 6,428,532 B1 | * | 8/2002 | Doukas et al. ................ 606/9 |
| 6,540,922 B1 | * | 4/2003 | de Cordemans et al. .... 210/695 |

FOREIGN PATENT DOCUMENTS

| | | |
|---|---|---|
| DE | 44 30 587 | 2/1996 |
| EP | 0 577 871 | 2/1994 |
| EP | 0 633 049 | 1/1995 |
| EP | 0 661 090 | 7/1995 |
| EP | 0 680 779 | 11/1995 |
| JP | 05/345192 | 12/1993 |
| WO | WO 80/00226 | 2/1980 |
| WO | WO 93/13674 | 7/1993 |
| WO | WO 98/01394 | * 1/1998 |

* cited by examiner

*Primary Examiner*—Peter A. Hruskoci
(74) *Attorney, Agent, or Firm*—Knobbe, Martens, Olson & Bear LLP

(57) ABSTRACT

A device for treating liquid medium has an ultrasound emitter located relative to a compartment of a container holding a liquid medium and a microbubble emitter located relative to the compartment. The ultrasound emitter emits high-frequency ultrasound between about 200 KHz and 10 MHz. The microbubble emitter emits bubbles with an average diameter of less than 1 mm.

23 Claims, 4 Drawing Sheets

DEVICE AND PROCESS FOR TREATING A LIQUID MEDIUM

CROSS-REFERENCE TO RELATED APPLICATION

This application is a continuation of and claims priority to U.S. patent application Ser. No. 09/214,398, filed Aug. 27, 1999, now U.S. Pat. No. 6,540,922 which is a National Phase application under 35 U.S.C. 371 of PCT/BE97/00078, filed Jul. 4, 1997, which claims priority to Belgian Patent Application 09600613, filed Jul. 4, 1996.

OBJECT OF THE INVENTION

The present invention relates to a novel device and to a process for treating a liquid medium, which are intended to remove microorganisms such as algae, bacteria, viruses, etc., and/or which are intended to allow a supersaturation with salts in the liquid medium.

TECHNOLOGICAL BACKGROUND

It is known to those skilled in the art that, depending on whether high-frequency or low-frequency ultrasound is used, different effects can be obtained on fluids. In order to obtain mechanical effects, low frequencies (generally between 16 and 100 kHz) are regularly used.

These mechanical effects, which are due to cavitation, make it possible, for example, to mix, emulsify and disperse heterogeneous substances, to degas the liquids, etc. These mechanical effects also create high shear effects in the liquids, which makes it possible, for example, to disrupt living cells present in this medium, to the point of rupturing the walls of cells of this type.

These same mechanical effects are also used to clean surfaces by the action of the microjets of liquid produced by the implosion of the cavitation bubbles. Similarly, the fact that various reactants can be mixed very efficiently is advantageously used to promote diffusion phenomena in various chemical reactions, especially heterogeneous reactions.

If high frequencies are used, generally of between 300 kHz and several MHz, the cavitation phenomena become relatively less energetic and the mechanical effects are more reduced than when low frequencies are used.

By applying high-frequency ultrasound to a liquid medium, the lifetime of the cavitation bubbles produced is greatly reduced, and chemical phenomena in a homogeneous phase take place, which are radically different from those observed when lower frequencies are applied.

One parameter which is specific to the use of high-frequency ultrasound is that, despite the low mechanical energy required to degas the solutions, the effect obtained is greater than when low-frequency ultrasound is applied, which itself requires more power.

PRIOR ART

It is known from different prior art documents that the use of ultrasound allows the detoxification of liquid media.

American patent U.S. Pat. No. 5,198,122 describes a process for detoxifying liquid and solid materials comprising various toxic organic compounds, which consists in adding to the medium a catalyst comprising a sodium borohydride or a lithium aluminium hydride to the said materials, which are then subjected to ultrasound so as to bring about cavitation in the mixture and to allow easier detoxification or extraction of the contaminating substances.

German patent application DE-4,407,564 describes a process for oxidizing organic substances or microorganisms, which is obtained by adding oxidizing agents (ozone) or phase-transfer catalysts.

Japanese patent application JP-930343777 (Marsima Aqua Syst. Corp.) describes a process and a purification installation for a water reservoir containing vegetable plankton. In the first reservoir of this installation, the vegetable plankton is inactivated using an ultrasound vibrator which induces cavitation in the water. The product of this treatment is then transferred into a second reservoir, in which predation of the inactivated vegetable plankton by animal plankton is promoted.

Similarly, it has been proposed in various documents (JP-900401407 (Ina Shokuhin Kogyo KK), JP-920035473 (Kubota Corp.), JP-920035472 (Kubota Corp.) and JP-920035896 (Kubota Corp.) to bring about the removal of organochlorine substances or to remove microorganisms by a cavitation phenomenon using ultrasound and injections of ozone, peroxides and/or catalysts.

Japanese patent application JP-820010627 (Hitachi Kiden Kogyo KK) describes a process for removing algal spores by a mechanical effect brought about by the use of high and low frequency ultrasound, inducing the sterilization and removal of the spores which become attached to plates and are then removed by the purifying effect of the low frequency ultrasound cavitation.

All of these previous examples use the mechanical effects of low frequency ultrasound.

It is known from the scientific publication by Pétrier C. et al. (Journal of Physical Chemistry, No. 98, 10514–10520 (1994)) that the sonochemical degradation of phenols in aqueous solutions varies as a function of the ultrasound emission frequency. According to that document, the degree of sonochemical degradation is thought to be directly associated with the presence in the solution of free radicals such as, for example, $H^-$, $^-OH$ and $HOO^-$, originating from the sonolysis of the water by ultrasound. According to that document, the production of these free radicals, in particular the $^-OH$ and $^-OOH$ radicals, is said to be greater by working with high frequency ultrasound emission.

As is seen in the illustrations in that document, the radicals produced by ultrasound induce a fluorescence whose distribution varies as a function of the conception and design of the apparatus, as well as of the ultrasound emission frequency. This fluorescence induced by the radicals produced by ultrasound is demonstrated by the addition of luminol to the aqueous composition.

However, that document does not in any way suggest that the oxidation phenomenon obtained by high frequency ultrasound could be used to attack microorganisms present in this aqueous medium and thus remove them.

American patent U.S. Pat. No. 2,717,874 describes a device for processing an aqueous medium comprising microorganisms, by adding chlorinated reagents. The said device comprises a bell (cell) which communicates with a reservoir of the aqueous medium to be treated, and contains a high frequency ultrasound emitter located at the base of the bell. In addition, the bell has a device for emitting air bubbles at the cone of the geyser.

Patent application WO 93/13674 describes a process for pasteurizing milk or milk-based products so as to remove a certain number of microorganisms such as bacteria, viruses, spores, etc. The device and the process described in that document are based on the use of the cavitation obtained at low frequencies and at high power during particularly long application times.

European patent application EP-A1-0,633,049 describes a process for treating a liquid by emitting an ultrasound field so as to separate the particles present in this liquid. That process uses high frequencies, which allow the separation of the micro-particles by standing-wave fields in which the position is modified by a phase or frequency variation, which entrains the particles which thus remain concentrated in nodes or antinodes. In the case of biological particles, this device makes it possible to create a bioreactor in which the solid particles of any nature remain confined in the ultrasound field, which allows filtration of the liquid medium. It should be pointed out that the device makes it possible to sterilize biological materials and to inactivate microorganisms.

American patent U.S. Pat. No. 4,961,860 describes a process for treating water, so as to remove the microorganisms present by means of ultrasound emission of low-frequency power. However, that device requires particularly large energy consumption in order to obtain a mechanical effect which removes the microorganisms.

AIMS OF THE INVENTION

The present invention is directed towards providing a device and a process which can neutralize, prevent the growth of and/or remove a certain number of undifferentiated animal cells, such as tumour cells and/or microorganisms, in particular algae, bacteria, viruses, etc., from a liquid medium in a simple and inexpensive manner, and which do not have the drawbacks of the prior art.

One specific aim of the present invention is to neutralize, prevent the growth of and/or remove the said undifferentiated cells or microorganisms, in particular algae, present in liquid media such as swimming-pool water, water towers, fishponds, aquariums or any other water reservoir, and by extension any industrial circuit, for example a cooling circuit, in which the quality of the water is particularly important, or physiological fluids such as blood or plasma, which can be extracted from and/or administered to man or animals.

The invention is also directed towards obtaining a device and a process which do not require the addition of additional chemical products needed to obtain the abovementioned effects in the media treated.

Another aim of the invention is to obtain a device and a process which do not consume much energy.

An additional aim of the present invention is to obtain a device and a process for treating a liquid medium with ultrasound without giving rise to a standing-field phenomenon.

A final aim of the present invention is to provide a device and a process for treating an aqueous medium, which makes it possible to supersaturate the liquid medium with salts, i.e. to obtain salt concentrations greater than the natural solubility of these salts in the aqueous medium.

CHARACTERISTIC FEATURES OF THE INVENTION

Figure 1:
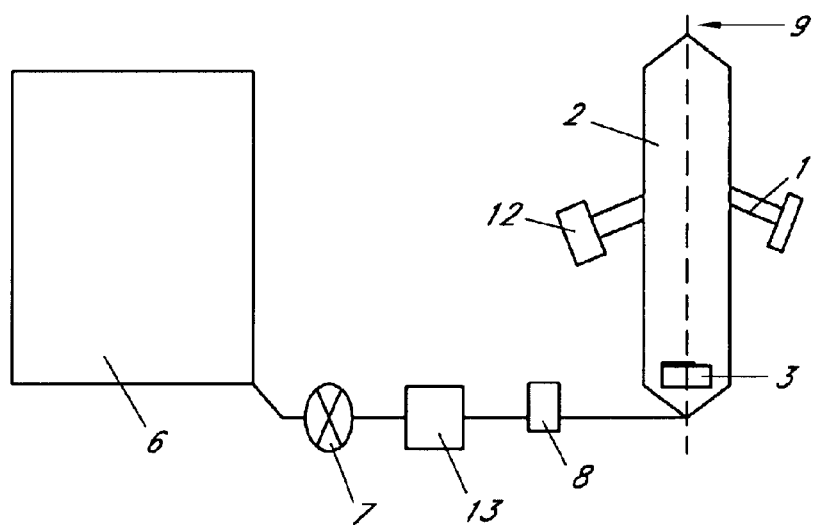
FIGS. 1 and 2 relate to a device for treating a liquid medium in the present invention.
Figure 2:
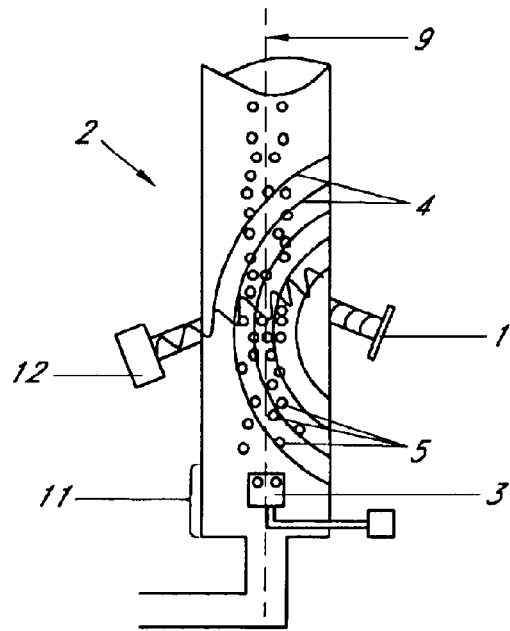

The present invention as represented in FIGS. 1 and 2 relates to a device or installation for treating a liquid medium, preferably an aqueous medium (which may contain undifferentiated cells or microorganisms), characterized in that it comprises a compartment 2, preferably of cylindrical shape or of rectangular cross-section, preferably communicating with a "reservoir" 6 of the liquid medium to be treated, the said compartment 2 containing (along its wall) one or more high-frequency ultrasound 4 emitters 1 which ultrasound is emitted into the compartment 2 (preferably into the centre of this compartment 2), and one or more gas microbubble 5 emitters 3, which are arranged so as to emit the gas microbubbles 5 into the ultrasound 4 field emitted in the compartment 2.

The term "microbubbles" is intended to refer to gas bubbles with an average diameter of less than 1 mm, preferably less than or equal to 50 $\mu$m, more particularly less than 30 $\mu$m.

The term "undifferentiated cells" is intended to refer to cells displaying a hyperproliferative effect, such as tumour cells, bone marrow cells or totipotent cells, in particular algal cells, etc.

The term "microorganisms" present in a liquid medium which it is desired to treat is intended to refer to any pathogenic or non-pathogenic microorganism which can give rise to harmful effects in man or animals or in installations for transporting and storing liquid media. Such microorganisms can be bacteria, viruses or algae. The definition of these microorganisms comprises unicellular and multicellular entities, in particular algae, which may be present in various liquid media, preferably aqueous media such as swimming pools, water reservoirs, aquariums, industrial cooling circuits such as cooling towers, etc.

The term "liquid medium" is also intended to refer to physiological liquids which may be administered to man or animals, or extracted from man or animals and reinjected therein after treatment (ex-vivo treatment of physiological liquids such as blood, serum, cephalorachidian fluid, etc.), as described in American patent U.S. Pat. No. 5,401,237 incorporated herein by way of reference.

The term "high frequencies" is intended to refer to frequencies of between 100 kHz and several MHz. Preferably, the high frequencies used are between 200 kHz and 10 MHz.

Preferably, the said emitter 3 of gas microbubbles 5 is arranged at the base 11 of the compartment 2, i.e. at the bottom of compartment 2, such that the microbubbles move by rising naturally or by entrainment of the gas in the flow of liquid.

Advantageously, the gas microbubbles are microbubbles of air, ozone or oxygen.

According to the invention, the said microorganisms appear to be removed by the production in their environment of radicals such as H$^-$, $^-$OH and HOO$^-$ which can also form H$_2$O$_2$, this molecule and/or these radicals being toxic to these microorganisms and thus bringing about their inactivation and/or destruction.

The species created are thought to be derived from the reactions of high-frequency ultrasound on the water molecule, possibly giving rise (in particular in the presence of oxygen) to the following reactions:

$$H_2O \rightarrow H^- + {}^-OH$$

$$H^- + O_2 \rightarrow HOO^-$$

$$HOO^- + HOO^- \rightarrow H_2O_2 + O_2,$$

$${}^-OH + {}^-OH \rightarrow H_2O_2$$

Advantageously, the energy required to produce the toxic species is reduced if the process is performed in the presence of these microbubbles.

The reason for this is that it would appear that the injection of microbubbles into the ultrasound field gives rise to an increase in the phenomenon of sonoluminescence, by superposition of the microbubbles onto the cavitation bubbles induced by the ultrasound, which appears to multiply the number of excited and toxic species.

This phenomenon is observed on a macroscopic level when the ultrasound treatment is synergistically combined with the presence of microbubbles of suitable size.

This phenomenon is emphasized by the fragmentation of the microbubbles 5 created when they pass into the ultrasound field 4, in particular when the device includes several successive emitters along the wall of the compartment 2, which ensure greater fragmentation of the microbubbles, in a progressive manner.

Figure 3:
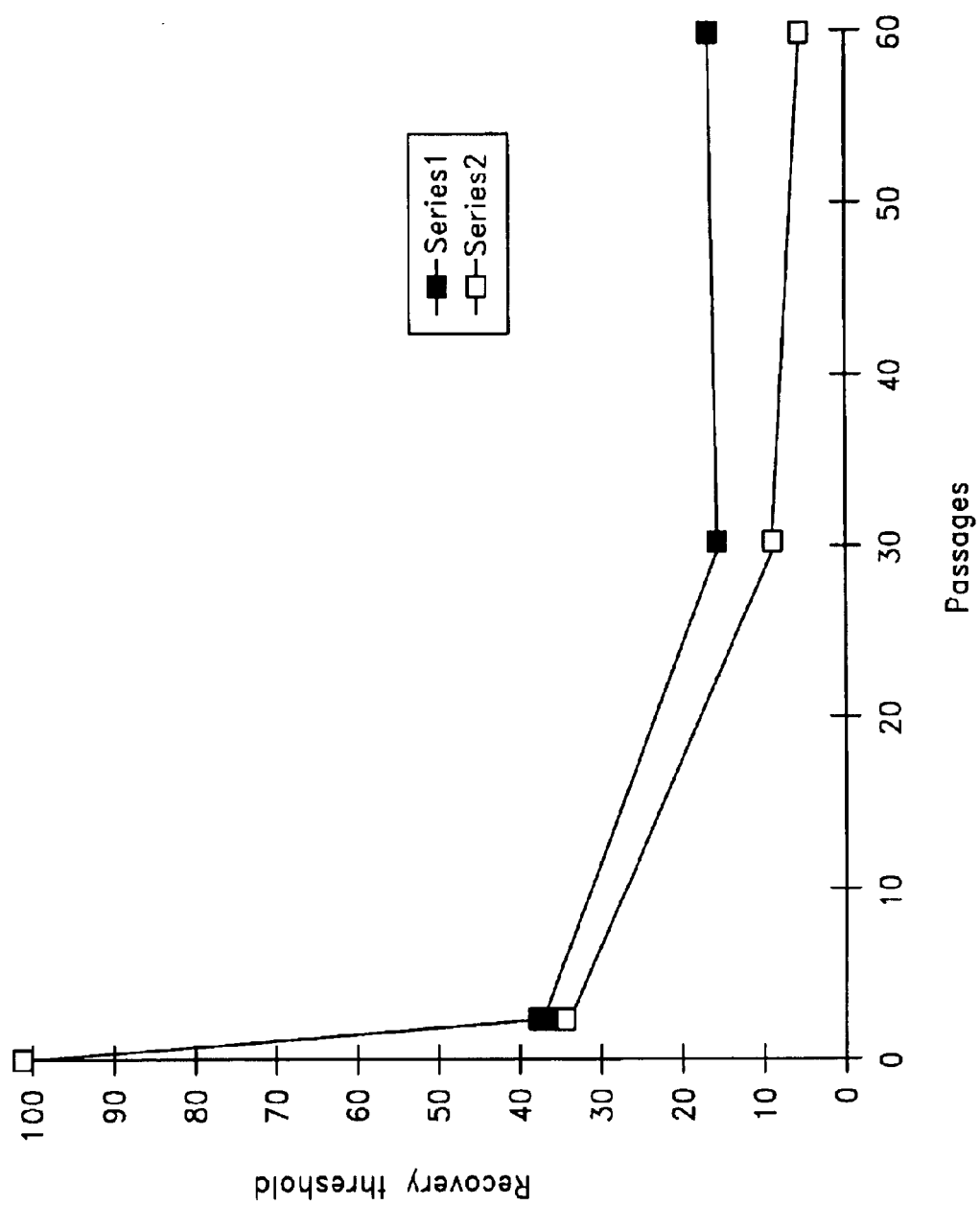
FIGS. 3 and 4 illustrate comparative tests with and without injection of microbubbles, respectively.
Figure 4:
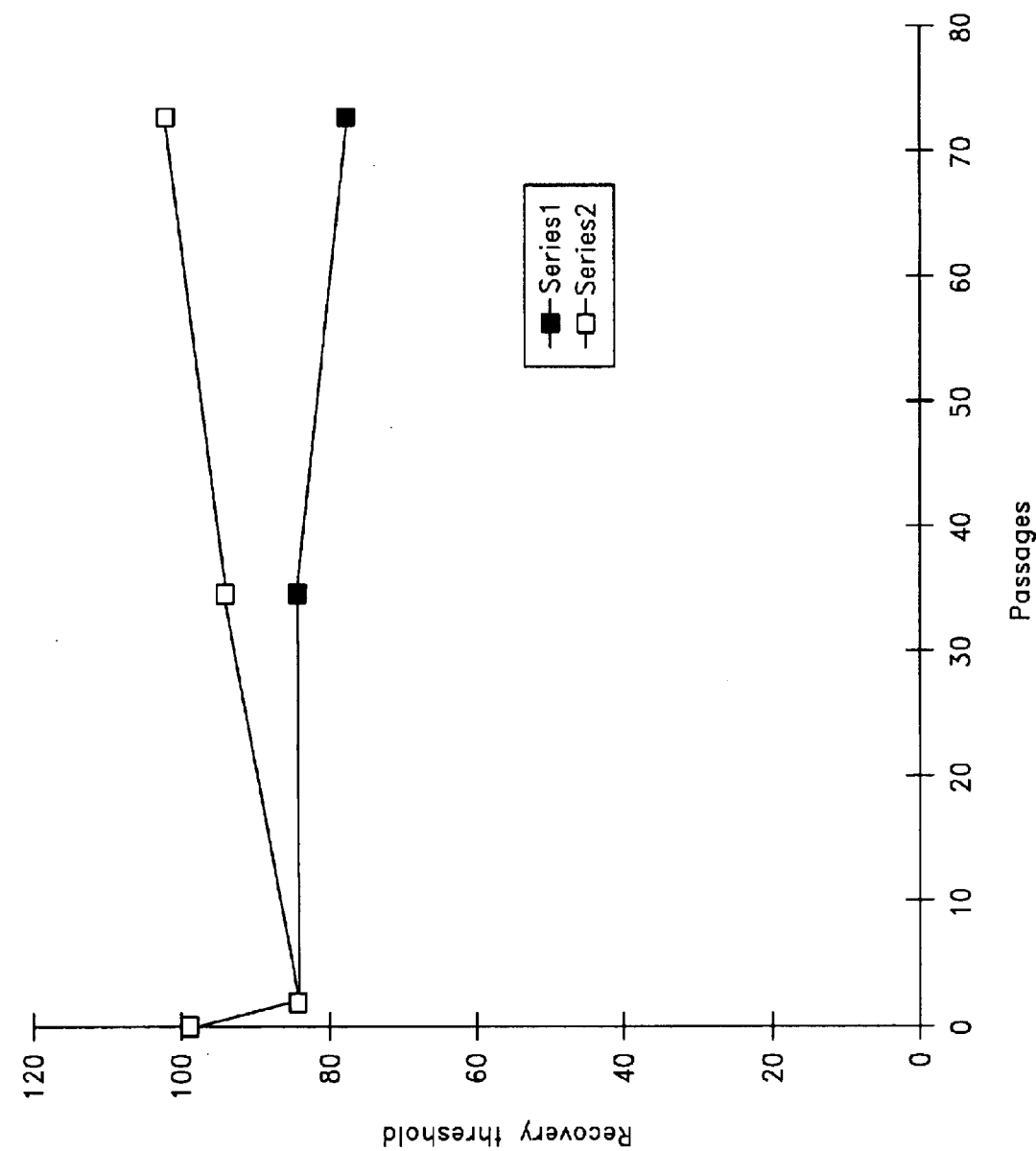
Figure 5:
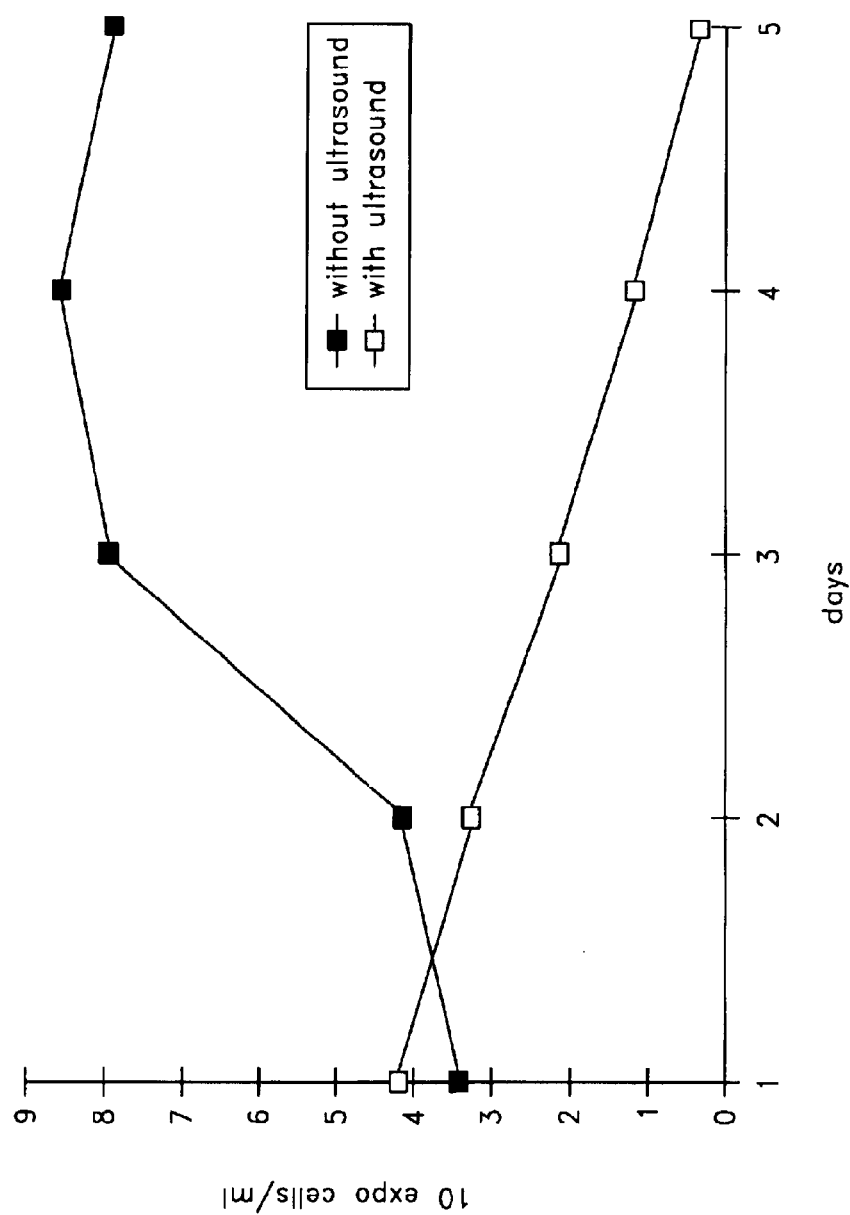
FIG. 5 illustrates treatments with and without ultrasound.

These characteristics are illustrated in particular by the comparative tests in the attached FIGS. 3 to 5.

FIGS. 3 and 4 summarize the counting of algae of the type *Selenastrum capricornutum*. It is observed that when these algae are placed under optimum culture conditions, their recovery threshold is inhibited when they are treated with the device of the invention (with injection of microbubbles (FIG. 3) and without injection of microbubbles (FIG. 4)). For a given ultrasound power, the efficacy of the treatment is proportional to the residence time in the compartment, and, consequently, inversely proportional to the flow rate.

FIG. 5 demonstrates, relative to a reference blank (treated with all the concentration, flow rate, temperature and bubbling conditions equal, but without ultrasound), the effect of the ultrasound. It is observed that a treatment with ultrasound but without injection of microbubbles does not give rise to an inhibition of growth or to a decrease in the number of algae in the liquid media.

In addition, the device has the advantage that there is no need to devote the ultrasound to specific zones, since it is observed that the treatment system functions by diffusing the products formed in situ (for example radicals and $H_2O_2$ formed) towards the reservoir 6 of aqueous medium to be treated.

In addition, the ultrasound 4 emitter 1 in the device of the invention is oriented so as not to give rise to any standing-wave phenomena, i.e. it is oriented obliquely relative to the axis 9 of the compartment 2 (acute angle not perpendicular to this axis 9) and relative to the flow of liquid and to the flow of microbubbles 5 (see FIG. 2). This characteristic makes it possible for all the microbubbles 5 in the compartment 2 to be treated in a statistically identical manner, without creating stationary zones in the said compartment 2.

According to a preferred embodiment of the invention, the device also comprises a light emitter 12 which emits into the compartment 2 in the ultrasound 4 field, i.e. an electromagnetic radiation emitter, most of the frequency of which radiation is in the visible range. However, for certain applications, in order to remove certain specific microorganisms, it may be advantageous also to emit electromagnetic radiation of which certain frequencies correspond to ultraviolet radiation (of UVA, UVB or UVC type) or other types of energy emission such as infrared, laser, microwaves, etc.

The reason for this is that the inventors have observed, unexpectedly, that a treatment comprising the emission of microbubbles into the fields combined with ultrasound and light radiation is particularly effective at inactivating and removing microorganisms, in particular algae, present in the liquid medium. The phenomenon of sonoluminescence can promote the production of extremely active oxygenated species such as the superoxide radical or singlet oxygen, which are responsible for a whole series of biochemical reactions which are extremely toxic for certain microorganisms.

It is known that such a phenomenon can take place in the presence of so-called photosensitizing molecules, so as to give rise to an antitumour action on certain cancer cells (Umemura S. I., Japanese J. of Cancer Res., 81, pp. 962–966 (1990)). Such molecules are, in particular, porphyrins, chlorines, tetracyclines, methylene blue, fluorescein, acridine, rhodamine, etc. These active agents are injected into the organism or administered orally and subsequently activated by sonoluminescence, and thus produce the singlet oxygen which in turn plays a fundamental role, in particular in biochemical processes due to oxidative stress. The action of singlet oxygen is to oxidize the various cell components, such as the proteins, lipids, amino acids and nucleotides.

According to the present invention, it is not always necessary to add a photosensitizing agent to the medium to be treated, since the inventors have observed, unexpectedly, that this effect can be produced in situ on certain microorganisms, in particular algae, or certain cells, in particular undifferentiated cells such as tumour cells present in physiological fluids such as blood, already containing these photosensitizing molecules.

When a human or animal physiological fluid is treated, the device of the present invention may not contain a reservoir 6 and can be directly connected to the human or animal body from which the physiological fluid is taken and reinjected by a process of extra-corporal treatment of the human or animal body.

According to a preferred embodiment of the invention, as represented in FIG. 1, the device comprises, placed between the reservoir 6 and the compartment 2, a means 13 for electromagnetic treatment of the aqueous medium. This means 13 is thus separate from the compartment 2 and placed upstream of it relative to the flow of the aqueous medium to be treated.

The expression "means for electromagnetic treatment of an aqueous medium" is intended to refer to any apparatus which allows the formation of crystals to be modified, or even directed (modification of the morphology of the crystals).

Such apparatus is described in particular in European patent application EP-0,515,346, incorporated herein by way of reference, which describes a generator for controlling the nucleation and/or growth of crystals and/or their morphology. That document describes a specific example for directing calcium carbonate crystals into a dendritic shape, these crystals being, in this case, in a shape which is incapable of forming tartar encrustations (in pipes, exchangers, etc.).

Such a means for electromagnetic treatment of the aqueous medium allows, when the said aqueous medium is subjected to the action of a field created between at least two transfer means (so as to modify the nucleation and/or formation and/or growth of crystals, in particular of calcium carbonate), at least one of the said transfer means receiving substantially rectangular electrical signals comprising a first phase in which the signal is close to a lower level and a second phase in which the signal is close to a higher level, the said signals having, when they are close to the lower level or to the higher level, a series of dampened variations.

Advantageously, the signals correspond to the superposition of a rectangular wave with a frequency of less than 100,000 Hz, preferably between 1000 and 30,000 Hz, and of a dampened sinusoidal wave with a frequency of less than 100,000 Hz, preferably between 1 MHz and 15 MHz, and the dampening of the sinusoidal wave is such that after 5 periods of the said wave, the amplitude of the variation is less than 10% of that of the initial variation.

In one specific embodiment of the invention, for each phase of the rectangular wave, this wave is combined with a single dampened sinusoidal wave, the frequency of the dampened wave being greater than that of the rectangular wave and the dampened wave being emitted for each phase of the rectangular wave, the lifetime of the dampened wave being between 10 ns and 500 µs, preferably between 100 ns and 100 µs.

In one specific embodiment, the potential difference existing between the lower level and the higher level of the rectangular wave is between 5 and 200 V, preferably between 12 and 60 V, while the dampened waves are waves whose variations are located within a band ranging between a minimum level and a maximum level, the potential difference between the two said levels being between 1 and 60 V, preferably between 10 and 35 V.

The said means for electromagnetic treatment of an aqueous medium can also be the apparatus as described in American patent U.S. Pat. No. 4,879,045, incorporated herein by way of reference.

The inventors have discovered, unexpectedly, that the device of the invention, comprising a means for electromagnetic treatment of the liquid medium located upstream of the elements for treating the aqueous medium with microbubbles in a high-frequency ultrasound field, makes it possible to obtain a wide range of supersaturation with salts in the liquid medium before the crystallization phenomenon appears.

The term "supersaturation with salts" is intended to refer to the possibility of increasing the concentration of salts in the aqueous medium (beyond the concentration corresponding to the solubility product of the salts) without precipitating the said salts.

For example, the said salts consist of calcium carbonate present in the aqueous medium, which may be supplied via a connection of the aqueous medium to water in the uptake and distribution network or by adding the said salts to the liquid medium.

This large amount of salts present in the aqueous medium can also be obtained by a partial evaporation of the water, this phenomenon being particularly important in cooling towers.

The liquid medium can also comprise a supersaturation with other salts, such as alkali metal or alkaline-earth metal phosphates or sulphates, etc.

The inventors have observed, unexpectedly, that it is possible to obtain a concentration of salts, in particular of calcium carbonate, in the treated liquid medium, which is 10 times as high as the saturation concentration (maximum dissolution before precipitation).

Advantageously, it is also observed that the water thus treated remains clear.

Such a device makes it possible to develop anti-tartar systems, to produce waters supersaturated with salts, to induce biotoxic effects on certain microorganisms due to the presence of water supersaturated with certain salts, etc.

Such a device also makes it possible to obtain concentrated media without precipitation and to generate specific chemical reactions by addition of reagents.

The inventors have discovered, unexpectedly, that in order to obtain this phenomenon of supersaturation with salts in the treated aqueous media at an optimum level, it is necessary for the electromagnetic treatment device to be separate from the compartment in which the emission of microbubbles in the ultrasound field takes place, and preferably for it to precede the emission.

The device according to the present invention can comprise, arranged between the reservoir 6 containing the liquid medium to be treated and the tube 2, a pump 7 for circulating the liquid medium, as well as means for recovering, preferably by filtration, centrifugation or precipitation (such as cyclones, etc.), the microorganisms and/or the salts present in the liquid medium.

Another aspect of the present invention relates to the use of the device according to the invention for neutralizing and/or removing the microorganisms, in particular algae, present in a liquid medium to be treated.

The expression "neutralization and/or removal of a microorganism" is intended to refer to the reduction or maintenance below a certain concentration level (which varies for each microorganism and each liquid medium) of the microorganisms liable to multiply in this liquid medium.

A final aspect of the present invention relates to the use of the device according to the invention to bring about a supersaturation with salts in the liquid medium, preferably in the aqueous medium, i.e. to obtain salt concentrations greater than the natural solubility of these salts in the liquid medium, preferably a concentration 5 times, or even 10 times, as high as the natural solubility of these salts.

The supersaturated media thus obtained can be used to bring about specific chemical reactions by addition of reagents, thus giving the products formed novel properties (size, shape, specific surface, etc.). The reagents added can be solid, liquid or gaseous or can consist of heterogeneous mixtures.

What is claimed is:

1. A device for treating a liquid medium, comprising:
   a reservoir for holding the liquid medium to be treated, the reservoir being in fluid communication with a compartment;
   an ultrasound emitter located relative to the compartment to emit ultrasound into the liquid medium in the compartment during use of the device, the ultrasound emitter emitting high-frequency ultrasound between about 100 kHz and 10 MHz, wherein the ultrasound emitter is oriented obliquely to the axis of the compartment such that the ultrasound emitted does not generate a standing wave phenomena in the liquid medium in the compartment; and
   a microbubble emitter emitting bubbles with an average diameter of less than 1 mm, the microbubble emitter being arranged relative to the compartment so as to emit microbubbles into the high-frequency ultrasound field emitted into the compartment during use of the device.

2. A device according to claim 1, wherein the average diameter of the microbubbles is less than 50 µm.

3. A device according to claim 1, wherein the microbubble emitter is placed at the base of the compartment and during use of the device the microbubbles move by either rising naturally or by entrainment of the gas microbubbles in the liquid medium.

4. A device according to claim 1, further comprising a light emitter located relative to the compartment to emit light into the ultrasound field in the compartment during use of the device, the light emitting electromagnetic radiation mainly in the visible range.

5. A device according to claim 1, further comprising a means for electromagnetic treatment of the liquid medium so as to modify at least one of the nucleation, formation and growth of salt crystals during use of the device, said means being placed between the reservoir and the compartment.

6. A device according to claim 1 further comprising one or more means for collecting any microorganisms and/or salts present in the treated liquid medium during use of the device.

7. A device for treating a liquid medium to neutralize, remove and/or prevent the growth of undifferentiated cells and/or of microorganisms present in the liquid medium comprising:
    means for placing the liquid medium in fluid communication with a compartment to place medium in the compartment;
    means for emitting high-frequency ultrasound between about 100 kHz and 10 MHZ into the medium in the compartment, wherein said means is oriented obliquely to the axis of the compartment such that the ultrasound emitted does not generate a standing wave phenomena in the liquid medium in the compartment; and
    means for emitting microbubbles with an average diameter of less than 1 mm, into the high-frequency ultrasound field emitted into the medium in the compartment.

8. A device according to claim 7, further comprising means for electromagnetic treatment of the medium so as to modify at least one of the nucleations, formation and growth of salt crystals in the medium.

9. A method for treating a liquid medium to neutralize, remove and/or prevent the growth of undifferentiated cells and/or of microorganisms present in the liquid medium comprising the steps of:
    placing the liquid medium in fluid communication with a compartment to place medium in the compartment;
    emitting high-frequency ultrasound between about 100 kHz and 10 MHz into the medium in the compartment with an ultrasound emitter oriented obliquely to the axis of the compartment such that the ultrasound emitted does not generate a standing wave phenomena in the liquid medium in the compartment; and
    emitting microbubbles with an average diameter of less than 1 mm, into the high-frequency ultrasound field emitted into the medium in the compartment.

10. A method according to claim 9, wherein the microorganisms are selected from the group consisting of bacteria, viruses and algae.

11. A method according to claim 9, wherein the undifferentiated cells are at least one of cancer cells and bone marrow cells.

12. A method according to claim 11, comprising the further step of adding reagents to the liquid medium to bring about one of a chemical reaction, precipitation reaction and crystallization reaction.

13. A method according to claim 9, comprising the further steps of providing a liquid medium containing salts, electromagnetically treating the medium so as to modify at least one of the nucleation, formation and growth of salt crystals in the medium, and bringing about a supersaturation of salts in the medium by the emitting ultrasound and microbubbles.

14. A method according to claim 9, wherein that the supersaturation with salts in the liquid medium comprises the steps of obtaining a salt concentration which is greater than the natural solubility of the salt in the liquid medium of at least 5 times as high as the natural solubility of the salt in the liquid medium.

15. A device for treating a liquid medium in an industrial circuit, comprising:
    a reservoir for holding the liquid medium to be treated, the reservoir being in fluid communication with a compartment;
    an ultrasound emitter located relative to the compartment to emit ultrasound into the liquid medium in the compartment during use of the device, the ultrasound emitter emitting high-frequency ultrasound between about 100 kHz and 10 MHz, wherein the ultrasound emitter is oriented obliquely to the axis of the compartment such that the ultrasound emitted does not generate a standing wave phenomena in the liquid medium in the compartment;
    a microbubble emitter emitting bubbles with an average diameter of less than 1 mm, the microbubble emitter being arranged relative to the compartment so as to emit microbubbles into the high-frequency ultrasound field emitted into the compartment during use of the device.

16. The device of claim 15, wherein the industrial circuit is a cooling circuit.

17. The device of claim 15, wherein the industrial circuit is a cooling tower.

18. The device of claim 15, further comprising a light emitter located relative to the compartment to emit light into the ultrasound field in the compartment during use of the device, the light emitting electromagnetic radiation mainly in the visible range.

19. A method for treating a liquid medium in an industrial circuit comprising:
    placing the liquid medium in a compartment;
    emitting high-frequency ultrasound between about 100 kHz and 10 MHz into the medium in the compartment with an ultrasound emitter oriented obliquely to the axis of the compartment such that the ultrasound emitted does not generate a standing wave phenomena in the liquid medium in the compartment; and
    emitting microbubbles with an average diameter of less than 1 mm, into the high frequency ultrasound field emitted into the medium in the compartment.

20. The method of claim 19, wherein the industrial circuit is a cooling circuit.

21. The method of claim 19, wherein the industrial circuit is a cooling tower.

22. The method of claim 19, wherein the liquid medium contains salts, the method further comprising:
    electromagnetically treating the medium so as to modify at least one of the nucleation, formation and growth of salt crystals in the medium; and
    supersaturating the salts in the medium by emitting ultrasound and microbubbles.

23. A method for treating cancer cells in a liquid medium comprising:
    emitting high-frequency ultrasound between about 100 kHz and 10 MHz into the medium with an ultrasound emitter; and
    emitting microbubbles with an average diameter of less than 1 mm, into the high-frequency ultrasound field emitted into the medium.

* * * * *